(12) United States Patent
Mullis

(10) Patent No.: US 8,591,910 B2
(45) Date of Patent: *Nov. 26, 2013

(54) CHEMICALLY PROGRAMMABLE IMMUNITY

(75) Inventor: Kary B. Mullis, Corona Del Mar, CA (US)

(73) Assignee: Altermune Technologies LLC, Corona Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/543,718

(22) Filed: Jul. 6, 2012

(65) Prior Publication Data

US 2012/0276136 A1    Nov. 1, 2012

Related U.S. Application Data

(63) Continuation of application No. 12/336,746, filed on Dec. 17, 2008, now Pat. No. 8,236,321, which is a continuation of application No. 11/606,564, filed on Nov. 30, 2006, now Pat. No. 7,850,975, which is a continuation of application No. 10/178,046, filed on Jun. 21, 2002, now abandoned, which is a continuation of application No. PCT/US00/35179, filed on Dec. 21, 2000.

(60) Provisional application No. 60/171,707, filed on Dec. 22, 1999.

(51) Int. Cl.
| | |
|---|---|
| *A61K 38/14* | (2006.01) |
| *A61K 39/00* | (2006.01) |
| *A61K 39/385* | (2006.01) |
| *C07K 9/00* | (2006.01) |
| *C07H 21/04* | (2006.01) |
| *C12N 15/115* | (2010.01) |

(52) U.S. Cl.
USPC ....... 424/193.1; 514/44 R; 530/322; 530/350; 536/23.1

(58) Field of Classification Search
None
See application file for complete search history.

(56) References Cited

U.S. PATENT DOCUMENTS

| | | | |
|---|---|---|---|
| 4,169,137 A | 9/1979 | Hirschfeld et al. | |
| 4,243,749 A | 1/1981 | Sadeh et al. | |
| 4,637,459 A | 1/1987 | Roussel | |
| 4,711,955 A | 12/1987 | Ward et al. | |
| 4,737,453 A | 4/1988 | Primus | |
| 4,940,670 A | 7/1990 | Rhodes | |
| 5,017,558 A | 5/1991 | Vyas | |
| 5,204,449 A | 4/1993 | Puri | |
| 5,218,088 A | 6/1993 | Gorenstein et al. | |
| 5,378,815 A | 1/1995 | Kramanovic et al. | |
| 5,475,096 A | 12/1995 | Gold et al. | |
| 5,637,459 A | 6/1997 | Burke et al. | |
| 5,683,867 A | 11/1997 | Biesecker et al. | |
| 5,869,232 A | 2/1999 | Sallberg | |
| 6,040,137 A | 3/2000 | Sallberg | |
| 6,054,312 A | 4/2000 | Larocca et al. | |
| 6,090,381 A | 7/2000 | Leung et al. | |
| 6,140,091 A * | 10/2000 | Raso et al. ................. | 435/188.5 |
| 6,232,071 B1 | 5/2001 | Hicke et al. | |
| 6,245,895 B1 | 6/2001 | Sallberg | |
| 6,248,332 B1 | 6/2001 | Romet-Lemonne et al. | |
| 6,261,774 B1 | 7/2001 | Pagratis et al. | |
| 6,280,932 B1 | 8/2001 | Parma et al. | |
| 6,280,943 B1 | 8/2001 | Drolet et al. | |
| 6,300,074 B1 | 10/2001 | Gold et al. | |
| 6,329,145 B1 | 12/2001 | Janjic et al. | |
| 6,331,394 B1 | 12/2001 | Ruckman et al. | |
| 6,344,318 B1 | 2/2002 | Gold et al. | |
| 6,344,321 B1 | 2/2002 | Rabin et al. | |
| 6,346,611 B1 | 2/2002 | Pagratis et al. | |
| 6,376,474 B1 | 4/2002 | Heilig et al. | |
| 6,387,620 B1 | 5/2002 | Smith et al. | |
| 6,395,888 B1 | 5/2002 | Biesecker et al. | |
| 6,579,696 B1 * | 6/2003 | Shekhani et al. ........... | 435/68.1 |
| 6,660,842 B1 | 12/2003 | Sallberg | |
| 6,867,289 B1 | 3/2005 | Gorenstein et al. | |
| 6,933,366 B2 | 8/2005 | Sallberg et al. | |
| 7,033,594 B2 | 4/2006 | Low et al. | |
| 7,112,328 B2 | 9/2006 | Marinkovich | |
| 7,422,746 B2 | 9/2008 | Mullis | |
| 2001/0031252 A1 | 10/2001 | Low et al. | |
| 2003/0017134 A1 | 1/2003 | Reiter | |

(Continued)

FOREIGN PATENT DOCUMENTS

| | | |
|---|---|---|
| EP | 0429816 | 5/1991 |
| EP | 1 242 115 B1 | 6/2009 |

(Continued)

OTHER PUBLICATIONS

Apostolopoulos et al (Nature Medicine, 1998, vol. 4, pp. 315-320).*

(Continued)

*Primary Examiner* — Karen Canella
(74) *Attorney, Agent, or Firm* — Davis Wright Tremaine LLP

(57) ABSTRACT

The present invention is related to methods and compositions that are capable of immediately immunizing a human or animal against any molecule or compound. The present invention comprises an immunity linker molecule with at least two sites; (1) a first binding site that binds to an immune system molecule in a human or animal that has been preimmunized against the first binding site, and (2) one or more second binding sites that bind specifically to a desired compound or molecule. The first binding site and the second binding site(s) are linked by a linker portion of the molecule.

18 Claims, 2 Drawing Sheets

(56) References Cited

U.S. PATENT DOCUMENTS

| | | |
|---|---|---|
| 2003/0017165 A1 | 1/2003 | Mullis |
| 2004/0185054 A1 | 9/2004 | Mullis |
| 2004/0253679 A1 | 12/2004 | Epstein et al. |
| 2006/0002891 A1 | 1/2006 | Pouletty |
| 2007/0148183 A1 | 6/2007 | Mullis |
| 2010/0247535 A1 | 9/2010 | Mullis |

FOREIGN PATENT DOCUMENTS

| | | | |
|---|---|---|---|
| WO | WO87/63444 | * | 10/1987 |
| WO | WO 92/08491 | | 5/1992 |
| WO | WO 95/05454 | | 2/1995 |
| WO | WO 95/29938 | | 11/1995 |
| WO | WO 97/37690 | | 10/1997 |
| WO | WO 01/25416 A1 | | 4/2001 |
| WO | WO 01/32207 | | 5/2001 |
| WO | WO 01/036448 | | 5/2001 |
| WO | WO 01/45734 A1 | | 6/2001 |
| WO | WO 2005/79423 A2 | | 9/2005 |

OTHER PUBLICATIONS abstract of Kilpatrick (Transfusion Medicine, 1997, vol. 7, pp. 289-294).*
abstract of Edwards et al (Jama, 1993, vol. 269, pp. 53-56).*
Office Action for U.S. Appl. No. 10/754,456; pp. 1-8; Apr. 1. 2008.
Alexander, H. et al.; "Altering the antigenicity of proteins"; Proc. Natl. Acad. Sci. USA, vol. 89, pp. 3352-2256; Apr. 1992.
Ahnert-Hilger, G. et al.; "Monoclonal Antibodies Against Tetanus Toxin and Toxoid"; Med Microbial Immunol; (1983) 172:123-135.
Bruno, John G. et al; "In vitro selection of DNA aptamers to anthraz spores with electrochemiluminescence detection"; Blosenors & Bioelectronics 14 (1999), pp. 457-464.
Carter, J. Mark; "Epitope Mapping of a Protein Using the Geysen (PEPSCAN) Procedure"; Methods in Molecular Biology vol. 36; Peptide Analysis Protocols; pp. 207-223 (1994).
Colas, Pierre et al.; "Genetic selection of peptide aptamers that recognize and inhibit cyclin-dependent kinase 2"; Nature; vol. 380; Apr. 11, 1996; pp. 548-550.
Edmundson, A.B. et al.; "Principles and Pitfalls in Designing Site-Directed Peptide Ligands"; Proteins: Structure, Function and Genetics; 16:3246-267 (1993).
Edmundson, Allen B. et al.; "Binding of peptides to proteins: an exercise in molecular design"; 1991 Host-guest molecular interactions: from chemistry to biology. Wiley, Chichester (Ciba Foundation Symposium 158); pp. 213-230.
Finberg, Robert W. et al.; "The Use of Antidiotypic Antibodies as Vaccines Against Infectious Agents"; CRC Critical Reviews in Immunology; vol. 7, Issue 4, (1987); pp. 269-284.
Geysen, H. Mario et al.; "Strategies for epitope analysis using peptide synthesis"; Journal of Immunological Methods, 102 (1987); pp. 259-274.
Geysen, H. Mario et al.; "Use of Peptide Synthesis to Probe Viral Antigens for Epitopes to a Resolution of a Single Amino Acid"; Proc. Natl. Acad. Sci USA; vol. 81 (Jul. 1984), pp. 3998-4002.
Geysen, H. Mario et al.; "Isotope or mass encoding of combinatorial libraries"; Chemistry & Biology; 1996, vol. 3, No. 8, pp. 679-688.
Glennie, Martin J. et al.,; "Preparation and Performance of Bispecific (F(ab'γ)$_2$ Antibody Containing Thioether-Linked Fab'γ Fragments"; Journal of Immunology; vol. 139, No. 7, Oct. 1, 1987, pp. 2367-237.
Jayasena, Sumedha D.; "Aptamers: An Emerging Class of Moleculares That Rival Antibodies in Diagnostics"; Clinical Chemistry; vol. 45; No. 9; (1999) pp. 1628-1650.
Ringquist, Steven et al.; "Anti-L-Selectin Oligonucleotide Ligands Recognize CD62L-Positive Leukocytes: Binding Affinity and Specificity of Univalent and Bivalent Ligands"; Cytometry; vol. 33, 1998; pp. 394-405.
Rodda, Stuart J. et al.; "Multipin Technology in the Preparation and Screening of Peptide Libraries"; Australasian Biotechnology 3, pp. 346-347 (1993).
Schultz, Jane S. et al.; "The Combinatorial Library: A Multifunctional Resource"; Biotechnol. Prog., 1996, 12, pp. 729-743.
Smith, George P.; "Surface presentation of protein epitopes using bacteriophage expression systems"; Current Opinion in Biotechnology (1991) vol. 2; pp. 668-673.
Tribbick, Gordon et al.; "Systematic fractionation of serum antibodies using multiple antigen homologous peptides as affinity ligands"; Journal of Immunological Methods, 139, (1991) pp. 155-16.
Valerio, Robert J. et al.; "Multipin peptide synthesis at the micromole scale using 2-hydroxyethyl methacrylate grafted polyethylene supports"; Int. J. Peptide Protein Res. 42, 1993, pp. 1-9.
Wagner, D.S.; "Ratio Encoding Combinatorial Libraries with Stable Isotopes and their Utility in Pharmaceutical Research"; Combinatorial Chemistry & High Throughput Screening, 1998, 1, pp. 143-153.
Weiner, George J. et al.; "Bispecific Anti-Idiotype/Anti-CD3 Antibody Therapy of Murine B Cell Lymphoma"; The Journal of Immunology; vol. 147, No. 11, Dec. 1, 1991, pp. 4035-4044.
Xu, Wei et al.; "Anti-peptide aptamers recognize amino acid sequence and bind a protein epitope"; Proc. Natl. Acad. Sci. USA; vol. 93, Jul. 1996, pp. 7475-7480.
Galili, Uri et al.; "α-Gal and Anti-Gal α1,3 Galactosyltransferase, α-Gal Epitopes, and the Natural Anti-Gal Antibody"; Subcellular Biochemistry; vol. 32, 1999, pp. 1-23.
Conrad, Richard et al.; "In Vitro Selection of Nucleic Acid Aptamers That Bind Proteins"; Methods in Enzymology, vol. 267, 1996, pp. 336-367.
Fitzwater, Tim et al.; "A SELEX Primer"; Methods in Enzymology, vol. 267, 1996, pp. 275-301.
Famulok, M., and Mayer, G.; "Aptamers as Tools in Molecular Biology and Immunology", Current Topics in Microbiology and Immunology, 1999, vol. 243, pp. 123-35; New York; Springer-Verlag, Inc.
Janczuk, AL. et al.; "alpha-Gal Oligosaccharides: Chemistry and Potential Biomedical Application"; Current Medicinal Chemistry; 1999, vol. 6, pp. 155-164.
PCT International Preliminary Report on Patentability in corresponding International application No. PCT/US2000/035179, mailed on Apr. 19, 2002, 5 pages.
Title: JP Office Action cited in JP App. No. JP2006-549430 Publ: Japanese Office Action pp. 1-3 Date: Jan. 4, 2011.
Title: Office Action for U.S. Appl. No. 12/685,257 Publ: U.S. PTO Office Action pp. 1-16 Date: Apr. 18, 2011.
Title: International Preliminary Report on Patentability and Written Opinion for WO 2005/079423 (PCT/US2005/000490) pp. 1-4 Date: Dec. 4, 2006.
Title: International Search Report for WO 2005/079423 (PCT/US2005/000490) pp. 1 Date: Nov. 30, 2005.
Title: International Search Report for WO 2001/45734 pp. 1-6 Date: Jun. 5, 2001.
Title: International Search Report and Written Opinion for International Application No. PCT/US2010/33716 pp. 1-6 Date: Aug. 6, 2010.
Title: EPO Office Action—Appl. No. 00990960.7 Publ: EPO Office Action pp. 1-7 Date: Oct. 17, 2005.
Title: EPO Supplementary Search Report—Appl. No. 00990960.7 Publ: EPO Search pp. 1-6 Date: Apr. 29, 2004.
Title: EPO Office Action—Appl. No. 00990960.7 Publ: EPO Office Action pp. 1-4 Date: Apr. 2, 2007.
Title: EPO Supplementary Search Report—Appl. No: 05751992.8 Publ: EPO Search pp. 1-4 Date: Oct. 6, 2008.
Title: EPO Office Action Action—Appl. No: 05751992.8 Publ: EPO Office pp. 1-7 Date: Dec. 3, 2008.
Title: AU Office Action—Appl. No. 2005213962 Publ: Australian Patent Office pp. 1-2 Date: Aug. 19, 2008.
Title: AU Office Action—Appl. No. 2005213962 Publ: Australian Patent Office pp. 1-4 Date: May 5, 2009.
Author: Brem et al. Title: Interstitial Chemotherapy with Drug Polymer Implants for the Treatment of Recurrent Gliomas Publ: J. Neurosurg. vol./Iss: 74 pp. 441-446 Date: Jan. 1, 1991.
Author: Davis et al. Title: Use of a High Affinity DNA Ligand in Flow Cytometry Publ: Nucleic Acids Research vol./Iss: 24(4) pp. 702-706 Date: Jan. 1, 1996.

(56) References Cited

OTHER PUBLICATIONS

Author: Herbert et al. Title: Dictionary of Immunology vol./Iss: 3rd Ed. pp. 3-4 Date: Jan. 1, 1985.
Title: EPO Office Action cited in 05751992.8 Publ: EPO Office Action pp. 1-6 Date Nov. 2, 2010.
Author: Nielsen et al. Title: Synthesis and Character of Dinucleoside Phosphorodithioates Publ: Tetrahedron Lett. vol./Iss: 29(24) pp. 2911-2914 Date: Jan. 1, 1988.
Title: Office Action for U.S. Appl. No. 10/754,456 Publ: U.S. PTO Office Action pp. 1-7 Date: Jun. 22, 2009.
Title: Office Action for U.S. Appl. No. 11/606,564 Publ: U.S. PTO Office Action pp. 1-14 Date: Jan. 29, 2009.
Title: Office Action for U.S. Appl. No. 11/606,564 Publ: U.S. PTO Office Action pp. 1-8 Date: Mar. 21, 2008.
Title: Office Action for U.S. Appl. No. 11/606,564 Publ: U.S. PTO Office Action pp. 1-6 Date: Feb. 23, 2010.
Title: Office Action for U.S. Appl. No. 10/754,456 Publ: U.S. PTO Office Action pp. 1-9 Date: Dec. 12, 2008.
Title: Office Action for U.S. Appl. No. 10/178,046 Publ: U.S. PTO Office Action pp. 1-6 Date: Jan. 11, 2006.
Title: Office Action for U.S. Appl. No. 10/696,770 Publ: U.S. PTO Office Action pp. 1-13 Date: Sep. 12, 2006.
Title: Office Action for U.S. Appl. No. 10/696,770 Publ: U.S. PTO Office Action pp. 1-10 Date: Jan. 17, 2008.
Title: Office Action for U.S. Appl. No. 10/754,456 Publ: U.S. PTO Office Action pp. 1-14 Date: Sep. 8, 2006.
Title: Office Action for U.S. Appl. No. 12/685,257 Publ: U.S. PTO Office Action pp. 1-34 Date: Nov. 5, 2010.
Title: Office Action for U.S. Appl. No. 10/754,456 Publ: U.S. PTO Office Action pp. 1-18 Date: Jun. 1, 2007.
Title: Office Action for U.S. Appl. No. 11/606,564 Publ: U.S. PTO Office Action pp. 1-13 Date: Jul. 22, 2009.
Author: Yang et al. Title: Deoxyxylothymidine 3'-O-Phosphorothioates: Synthesis, Stereochemistry And Stereocontrolled Incorporation Into Oligothymidylates Publ: J. Bioorganic & Med. Chem. Lett. vol./Iss: 7 pp. 2651-2656 Date: Jan. 1, 1997.
United States Patent and Trademark Office (USPTO), Non-Final Office Action, issued in corresponding U.S. Appl. No. 12/685,257, mailed Dec. 30, 2011, 17 pages.
Title: EPO Office Action cited in 05751992.8 Publ: EPO Office Action pp. 1-6 Date: Nov. 2, 2010.
Berzofsky and Berkower, "Immunogenicity and Antigen Structure", in: *Fundamental Immunology*, 3rd Ed., 1993, p. 235, W.E. Paul, Ed.
United States Patent and Trademark Office (USPTO), Non-Final Office Action, issued in corresponding U.S. Appl. No. 13/567,930, mailed on Mar. 14, 2013, 33 pages.

\* cited by examiner

Fig_1

CHEMICALLY PROGRAMMABLE IMMUNITY

This application is a continuation of U.S. patent application Ser No. 12/336,746, filed Dec. 17, 2008, which is a continuation of U.S. patent application Ser. No. 11/606,564, filed Nov. 30, 2006, now issued U.S. Pat. No. 7,850,975, which is a continuation of U.S. patent application Ser. No. 10/178,046, filed Jun. 21, 2002, now abandoned, which is a continuation of International Patent Application No. PCT/US2000/035179, filed Dec. 21, 2000, which application claims the benefit of U.S Provisional Application No. 60/171,072, filed Dec. 22, 1999, each of which is hereby incorporated by reference in its entirety.

FIELD OF THE INVENTION

The present invention relates to methods and compositions for providing immediate immunity to any desired antigen. The present invention also provides methods and compositions for treating a wide variety of diseases without having to wait for an immune response to be mounted by the human or animal being exposed to the disease.

BACKGROUND OF THE INVENTION

The term "antigen" is defined as anything that can serve as a target for an immune response. The immune response can be either cellular or humoral. The term "vaccine" is defined herein as a suspension or solution of antigenic moieties, usually consisting of infectious agents, or some part of the infectious agents, that is injected into the body to produce active immunity. The antigenic moiety making up the vaccine can be either a microorganism or a natural product purified from a microorganism, a synthetic product or a genetically engineered protein, peptide, polysaccharide or similar product. The term "cell mediated immunity" is defined as an immune response mediated by cells rather than by antibody. It includes, but is not limited to, delayed type hypersensitivity and cytotoxic T cells. The term "adjuvant" as used herein is any substance whose admixture with an injected immunogen increases or otherwise modifies the immune response. A "hapten" is defined antibodies or T cells, but the hapten itself is usually not immunogenic. Most haptens are small molecules or small parts of large molecules, but some macromolecules can also function as haptens. The term "conjugation" is defined herein as the covalent or other form of linking two or more molecules. It can be accomplished either by chemical means or in vivo by biologic means such as genetic engineering.

The process of immunization has been used for over a hundred years to protect humans and animals against disease. The process generally comprises injecting an antigen that is related to the pathogen in the human or animal and waiting an appropriate amount of time, allowing the human or animal in which the pathogen was injected to mount an immune response. The time required for mounting an immune response normally is between approximately two weeks and several months for most antigens. In most cases, a booster administration of the antigen is required to maintain the immune response. This booster is normally given weeks or months after the initial administration of the antigen. Thus, immunization is of little use for immediate treatment of a disease.

A separate immunization procedure must be made for each pathogen, although in some cases several antigens are included in a single vaccine. Every immunization carries with it a certain amount of risk that must be considered before any immunization is recommended on a wide-scale basis.

What is needed is a method of immunizing a human or animal that can result in an immediate immune response. In addition, a method of immunizing a human or animal by a single immunization would greatly reduce the inherent risks in the vaccination procedure.

SUMMARY OF THE INVENTION

The present intention provides methods and compositions for the immediate and specific immunization of a human or animal against a pathogen or other undesired substance. The present invention, in one embodiment, is designated an "immunity linker molecule" and comprises a molecule with multiple sites; a first binding site on the compound that is antigenic and is capable of mounting an immune response in a human or animal. After immunization of the human or animal, first binding site will then bind specifically to an antibody or other immune molecule that was induced by the immunization process. The molecule has a second binding site or sites that are capable of binding to one or more designated compounds. The present invention also includes a compound that contains only the first binding site or immunogenic site that is present in the immunity linker molecule. This compound that contains only the first binding site or antigenic site is designated herein as "the immunizing molecule".

According to the present invention, the immunity linker molecule can be made in several ways. The immunizing molecule with the first binding site can be physically linked or conjugated to the molecule with the second binding sites to the pathogen or other undesired substance. In another embodiment, the immunity linker molecule can be produced or manufactured as a single molecule containing the first binding site or immunizing site and the second binding sites. The immunity linker molecule can be any type of compound including protein, nucleic acid or a combination thereof. The first binding sight can be a hapten that is conjugated to a larger molecule.

In practicing the present invention, the human or animal is first immunized conventionally against the immunizing molecule. This process includes administering the molecule to the human or animal and then waiting an appropriate amount of time for an immune response to be mounted in the human or animal. If necessary, the immunizing molecule can be administered with an adjuvant and/or a booster may be given to the animal at appropriate times. These methods of immunizing a human or animal are well known to one of ordinary skill in the art. The human or animal that has been immunized against the immunizing molecule now has antibodies that will bind the immunizing molecule when it is present in the blood or other fluid.

When the preimmunized human or animal is challenged with a pathogen or toxic substance, an immunity linker molecule that contains a binding site to the pathogen or toxic substance is administered to the human or animal. The immunity linker molecule binds at one site to the antibody that was previously induced, and binds to the pathogen at the second site thereby providing an immune complex of the antibody bound to the immunity linker molecule which is now bound to the pathogen. The body now recognizes the immune complexes and processes them in a normal manner.

Accordingly, it is an object of the present invention to provide a method and composition for the immediate and specific immunization of a human or animal.

It is yet another object of the present invention to provide a method and composition for immediately immunizing an immunologically naive human or animal.

It is another object of the present invention to provide a method and composition that enables one to quickly and easily select a desired antigen and immediately immunize the human or animal against that antigen.

Another object of the present invention is to provide a method and composition that will only require a single immunization to protect against a wide variety of pathogens and toxic substances, thereby reducing the risks of multiple vaccinations.

Yet another object of the present invention is to provide a method and composition that will allow health care professionals to immediately immunize a patient against a wide variety of pathogens and/or toxins.

These and other objects, features and advantages of the present invention will become apparent after a review of the following detailed description of the disclosed embodiment.

DETAILED DESCRIPTION OF THE INVENTION

Figure 1:
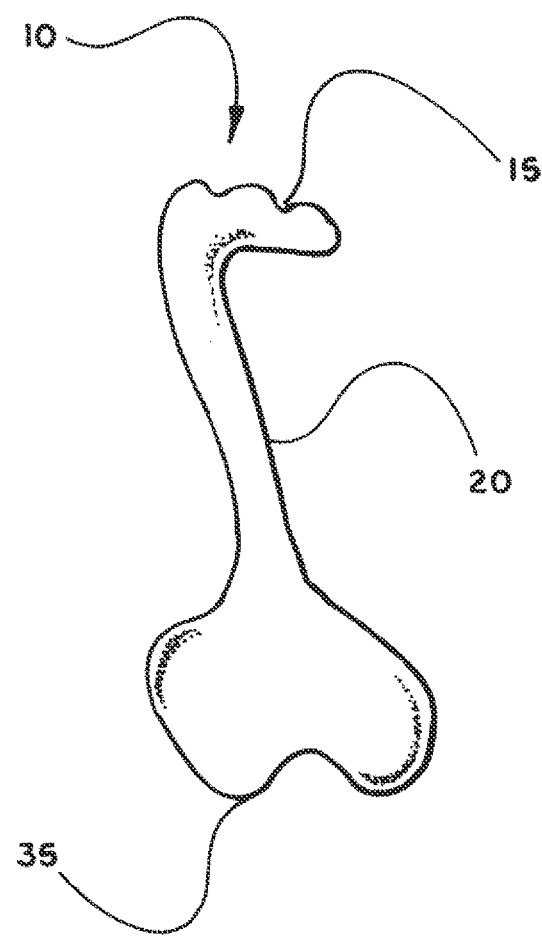
FIG. 1 illustrates the structure of the immunity linker molecule.
Figure 2:
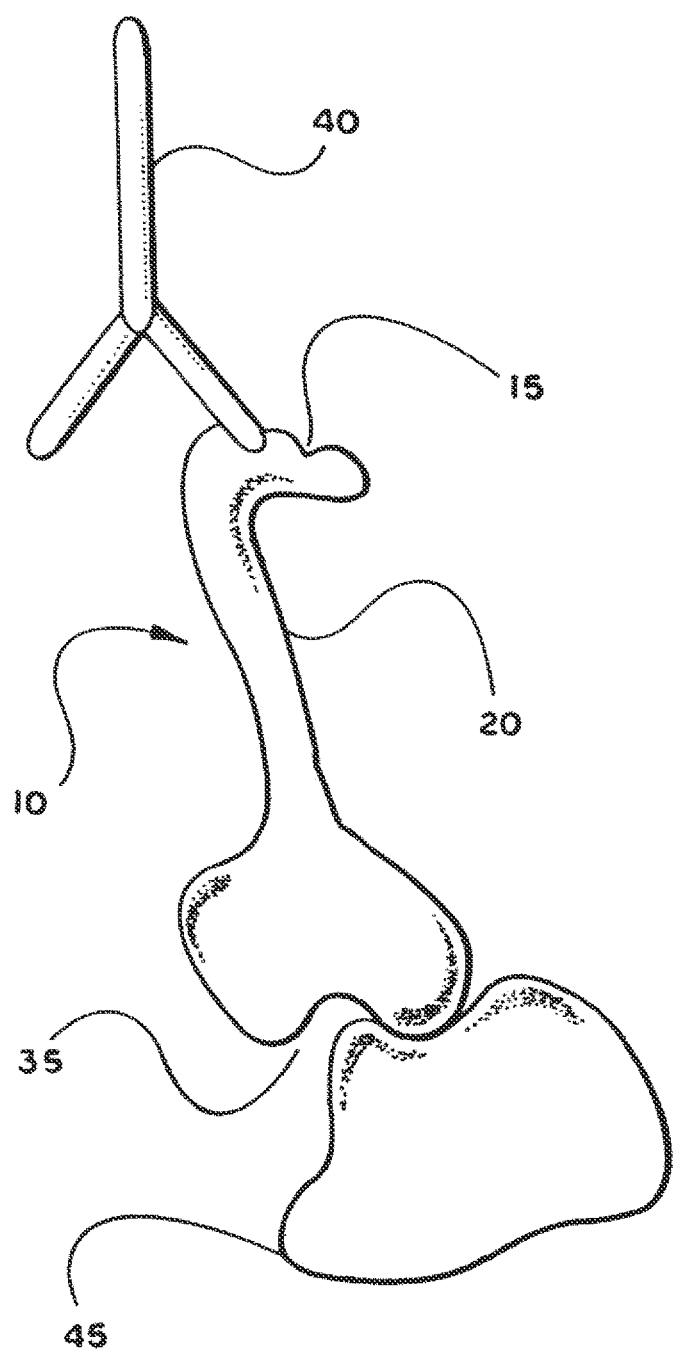
FIG. 2 illustrates the immunity linker molecule bound at one site to an antibody and, at a second site, to a desired molecule, thereby forming an immune complex.

The present invention is related to methods and compositions that are capable of immediately immunizing a human or animal against any molecule or compound. The present invention comprises an immunity linker molecule with at least two sites; (1) a first binding site that binds to an immune system molecule in a human or animal that has been preimmunized against the first binding site, and (2) one or more second binding sites that bind specifically to a desired compound or molecule. The first binding site and the second binding site(s) are linked by a linker portion of the molecule.

The present invention comprises methods and compositions for the immediate and specific immunization of a human or animal against a pathogen or other undesired substance. According to the present invention, a human or animal can be immediately immunized against a chosen antigen simply by administering to the human or animal the immunity linker molecule with the appropriate second binding site. According to the present invention, one can provide immediate immunity to any chosen antigen on the basis of the pre-existing immunity to the immunizing molecule by administration of a synthetic chemical linker.

In practicing the present invention, the human or animal is first immunized conventionally against the immunizing molecule. This process includes appropriately administering the molecule to the human or animal and then waiting an appropriate amount of time for an immune response to be mounted in the human or animal. The preferred method of administering the immunizing molecule is by injection. If necessary, the immunizing molecule can be administered with an adjuvant and/or a booster may be given to the animal at appropriate times. These methods of the immunizing a human or animal are well known to one of ordinary skill in the art. The human or animal that has been immunized against the immunizing molecule now has antibodies that will bind the immunizing molecule when it is present in the blood or other bodily fluid.

The immunizing molecule optionally can be administered with agents such as adjuvants, preservatives, diluents, emulsifiers, stabilizers, and other known components that are known and used in immunization procedures in the prior art. Any adjuvant system known in the art can be used in the composition of the present invention. Such adjuvants include, but are not limited to, Freund's incomplete adjuvant, Freund's complete adjuvant, polydispersed β-(1,4) linked acetylated mannan ("Acemannan"), Titermax® (polyoxyethylene-polyoxypropylene copolymer adjuvants from CytRx Corporation), modified lipid adjuvants from Chiron Corporation, saponin derivative adjuvants from Cambridge Biotech, killed *Bordetella pertussis*, the lipopolysaccharide (LPS) of gram-negative bacteria, large polymeric anions such as dextran sulfate, and inorganic gels such as alum, aluminum hydroxide, or aluminum phosphate. A preferred adjuvant system is Freund's incomplete adjuvant. Another preferred adjuvant system is Freund's complete adjuvant. The method of immunization and the adjuvants used are not critical to the invention. Thus, any method known in the art can be used, and any adjuvant system known in the art can be used.

According to the present invention, immediate immunity to, for example, a pathogen, can be established in a human or animal that is immunologically naive to the pathogen by administering to the human or animal that has been immunized against the immunizing molecule the immunity linker molecule that contains a binding site to the pathogen. The immunity linker molecule binds at one site to the antibody that was previously induced, and binds to the pathogen at the second site, thereby providing an immune complex of the antibody bound to the immunity linker molecule which is now bound to the pathogen. The body now recognizes the immune complexes and processes the complexes in a normal manner.

According to the present invention, the immunity linker molecule can be made in several ways. The immunizing molecule can be physically linked or conjugated to the molecule with the binding sites to the desired substance. In another embodiment, the immunity linker molecule can be produced or manufactured as a single molecule containing the multiple sites. In yet another embodiment, the immunity linker molecule consists of two active ends connected together by a rigid or flexible spacer such as a double helical region of RNA. The purpose of the spacer is to hold the two ends of the linker together, while preventing them from interacting.

The immunity linker molecule can be a protein, peptide, or nucleic acid molecule or any combination thereof, including, but not limited to, RNA molecules, DNA molecules or derivatives thereof. Preferably, the immunity linker molecule is comprised of RNA molecules and are produced according to the SELEX process. This process is described completely in the list of references attached hereto and are included herein by reference in their entirety.

The immunity linker molecule is shown schematically in FIG. 1. The immunity linker molecule 10 comprises a first binding site 15 which is antigenic, a linking portion of the molecule 20 and a second binding site 35 that is capable of binding a specific molecule. The second binding site 35 site or sites are preferably aptamers that have been produced by the SELEX process. However, it is to be understood that the second binding site does not have to be an aptamer, but can be any type of molecule that has the desired physical attributes, i.e., the second binding site being capable of binding to a specific molecule. It is to be understood that the immunity linker molecule can have more than one binding site to a single substance or can have multiple binding sites against multiple substances. The linking portion of the molecule links the first binding site 15 and the second binding site 35. The linking portion 15 of the molecule can be double stranded nucleic acid, but other linking molecules can be used in the present invention. FIG. 2 schematically shows the immunity linker molecule with an antibody 40 bound to the first binding site 15 of the molecule and a molecule 45 bound to the second binding site 35 on the immunity linker molecule 10.

It is to be understood that the immunity linker molecule can be any type of molecule that is capable of being manipulated so that it is capable of (1) mounting an immunity response, and (2) binding a desired molecule or molecules. The preferred type of compound is nucleic acid or, preferably, modified nucleic acid such as 2'-fluoro- or 2'-amino-2'-deoxypyrimidine containing nucleic acids. Nucleic acids using these bases are much more stable than naturally occurring nucleic acids. (See Aptamers as tools in molecular biology and immunology, M. Famulok and G. Mayer, Cur. Top. Micro. Immunobiol., 1999, 243, 123-146.)

The immunity linker molecule can be administered to a patient intramuscularly, subcutaneously, orally, intravenously, or through the mucosal membranes. The immunity linker molecule can be use in immunizing a human or animal against a wide variety of substrates, including, but not limited to, bacteria, fungi, viruses, toxic substances, and drugs.

The present invention is particularly useful in the military where troops may be unexpectedly exposed to a pathogen, toxin, or to a toxic chemical substance. Military personnel are preimmunized against the immunizing molecule, i.e., that portion of the immunity linker molecule that binds to the antibody. Then, if the military personnel are unexpectedly challenged with a pathogen, the appropriate immunity linker molecule can be administered to the military personnel, thereby immediately protecting them against the pathogen or other toxic substance. The present invention can be used to prevent and/or treat organisms including, but not limited to, anthrax, dengue virus, or Marburg virus.

Likewise, pharmacies can have a library of different immunity linker molecules available for a variety of different pathogens and toxic substances. If the patient has been preimmunized against the immunizing portion of the linker, then he or she will be immediately immunized against the pathogen or toxic substances.

It should be understood, of course, that the foregoing relates only to preferred embodiments of the present invention and that numerous modifications or alterations may be made therein without departing from the spirit and the scope of the invention as set forth in this disclosure.

The invention claimed is:

1. An immune-diverting composition comprising an immunity linker molecule comprising
    a first binding site that when administered to an individual is capable of binding to an antibody produced from a pre-existing immunity within the individual specific for a first compound or molecule, and
    a second binding site comprising a nucleic acid aptamer or a modified nucleic acid aptamer that is capable of binding to a target, wherein the first compound or molecule and the target are not the same.

2. The immune-diverting composition of claim 1, wherein the composition comprises an amount of the immunity linker molecule effective to provide substantially immediate immunity to the target.

3. The immune-diverting composition of claim 1, wherein the pre-existing immunity is induced by an immunizing molecule and optionally an adjuvant or a booster.

4. The immune-diverting composition of claim 1, wherein the immunity linker molecule comprises more than one second binding site.

5. The immune-diverting composition of claim 4, wherein the binding sites differ in specificity for targets.

6. The immune-diverting composition of claim 1, wherein the aptamer comprises a modified nucleic acid aptamer, and wherein the modified nucleic acid comprises 2'-fluoro or 2'-amino-2'deoxypyrimidine.

7. The immune-diverting composition of claim 1 further comprising a linking portion linking the first and second binding sites.

8. The immune-diverting composition of claim 7, wherein the linking portion comprises a rigid or flexible spacer.

9. The immune-diverting composition of claim 8, wherein the spacer is double stranded nucleic acid.

10. The immune-diverting composition of claim 1, wherein the immunity linker further comprises a protein, a peptide, a nucleic acid, or a combination thereof.

11. The immune-diverting composition of claim 1, wherein the target comprises a microorganism, a pathogen, a toxic substance, or a drug.

12. The immune-diverting composition of claim 11, wherein the microorganism is a bacterium, a virus, or a fungus.

13. The immune-diverting composition of claim 1, wherein the target comprises anthrax or a dengue virus.

14. The immune-diverting composition of claim 1, wherein the individual is unable to mount an effective immune response to the target compound or molecule prior to administration of the composition.

15. The immune-diverting composition of claim 1, wherein the composition is in a form suitable for at least one administration mode selected from the group consisting of intravenous administration, intramuscular administration, subcutaneous administration, oral administration, and mucosal administration.

16. A method of establishing substantially immediate immunity to a target in an individual comprising, wherein the method comprises administering to the individual an effective amount of the immune-diverting composition of claim 1.

17. The method of claim 16, wherein the individual is unable to mount an effective immune response to the target prior to the administering step.

18. The method of claim 16, wherein the immunity to the target is a cellular or humoral immunity.

* * * * *